United States Patent [19]

Reichert et al.

[11] Patent Number: 5,972,331
[45] Date of Patent: Oct. 26, 1999

[54] CRYSTALLINE INTERFERON ALPHA FOR PULMONARY DELIVERY AND METHOD FOR PRODUCING THE SAME

[75] Inventors: Paul Reichert, Montville, N.J.; Patricia C. Weber, Yardley, Pa.; Rowena F. Choudrie, Edison, N.J.; Bruce O. Stuart, Still Water, N.J.; Tattanahalli Nagabhushan, Parsippany, N.J.; Ashit Ganguly, Upper Montclair, N.J.

[73] Assignee: Schering Corporation, Kenilworth, N.J.

[21] Appl. No.: 08/577,585

[22] Filed: Dec. 22, 1995

[51] Int. Cl.$^6$ .................................. A61K 45/05
[52] U.S. Cl. .................. 424/85.1; 424/85.4; 424/85.7; 530/351
[58] Field of Search ............ 530/351; 424/85.1, 424/85.4, 85.7

[56] References Cited

U.S. PATENT DOCUMENTS

| | | | |
|---|---|---|---|
| 2,882,203 | 4/1959 | Petersen et al. | 530/351 |
| 4,672,108 | 6/1987 | Kung et al. | 530/351 |
| 5,441,734 | 8/1995 | Reichert et al. | 530/351 |
| 5,460,956 | 10/1995 | Reichert et al. | 530/351 |
| 5,503,828 | 4/1996 | Testa et al. | 530/351 |

FOREIGN PATENT DOCUMENTS

| | | | |
|---|---|---|---|
| 0 257 956 | 2/1988 | European Pat. Off. | 530/351 |
| 91/16038 | 10/1991 | WIPO | 530/351 |

OTHER PUBLICATIONS

Platz et al., Caplus # 192: 28202

*Primary Examiner*—Cecilia J. Tsang
*Assistant Examiner*—Patrick R. Delaney
*Attorney, Agent, or Firm*—J. P. McLaughlin

[57] ABSTRACT

A method to prepare crystalline interferon alpha suitable for aerosol formulation either for systemic or topical (inhaled) drug delivery. The bioavailable interferon is in the form of crystalline submicrometer particles having a predetermined medium diameter.

19 Claims, No Drawings

CRYSTALLINE INTERFERON ALPHA FOR PULMONARY DELIVERY AND METHOD FOR PRODUCING THE SAME

BACKGROUND OF THE INVENTION

Polypeptides and proteins have limited modes of administration. Transdermal or oral delivery is difficult because of the sheer size of proteins and polypeptides (>7,000 MW) and their instability in the gastrointestinal environment. In general, protein drugs are administered either by subcutaneous (s.c.) or intravenous (i.v.) injection usually in hospital or clinical settings. Proteins (<30,000 mw) injected s.c. or i.v. have serum half lives in duration of hours. Limitations in the mode of administration and serum half-life have limited the utility of protein therapeutics. There is a need for more effective and well-tolerated methods for the delivery of proteins and peptides. A possible mode of administration of a protein is via the lungs. There is a need for novel and effective methods for delivering therapeutic proteins to the lungs.

SUMMARY OF THE INVENTION

The present invention fills this need by providing for a crystalline interferon alpha-2 composition comprised of crystalline interferon alpha-2 particles having a range of diameters of from 0.7 $\mu$m (micrometer) to about 7.0 $\mu$m, preferably less than 5 $\mu$m and a pharmaceutically acceptable carrier which can be delivered in an aerosol mist to the lungs of an individual.

The present invention further provides for a method for preparing a suspension of crystalline interferon alpha-2 particles wherein the particles have a range of diameters of 0.7 to 7 $\mu$m comprising crystallizing interferon alpha-2 in solution to form a suspension of crystalline interferon alpha-2. The suspension is then mixed so as to produce a homogenous suspension of crystalline interferon alpha-2. The homogenous suspension of crystalline interferon particles is sedimentated under conditions wherein only crystalline interferon alpha particles having a range of diameters of from 0.7 to 7.0 $\mu$m are present in a supernatant suspension. Preferably the crystalline interferon alpha-2 particles have an average diameter of less than about 5 $\mu$m.

In a preferred embodiment, the solution of interferon alpha-2 is agitated during crystallization, thereby producing a large number of relatively smaller crystalline particles. The agitation can be by mechanical, sonic or other known means of agitation. The resultant suspension is allowed to settle such that particles having a diameter greater than about 7.0 $\mu$m settle to a bottom pellet layer and particles having an average diameter of less than 7.0 $\mu$m remain in a supernatant suspension.

DETAILED DESCRIPTION OF THE INVENTION

The teachings of all U.S. patents and patent applications cited herein are incorporated in their entirety by reference.

A crystalline suspension is prepared from an interferon solution using a temperature induction method followed by a separation process using fractional sedimentation. Submicrometer crystals in the range of 780 nanometers are produced which can be utilized to target either the upper or lower respiratory tract. Preferably, nebulization of submicrometer crystals will result in deposition of interferon in the pulmonary region of the lung. Crystalline suspensions offer the advantage over conventionally prepared dry powders which are manufactured in either jet milling or spray drying processes where degradation, oxidation or agglomeration may occur. Crystalline particles have the advantage of predictable properties of uniformity, homogeneity, stability, bioavailability and dissolution. We have identified formulations including surfactants compatible with conventional nebulizers. These crystals are heat stable and can potentially be suitable for delivery via ultrasonic or airjet nebulizer devices as well as metered dose inhalers. This is the first report of a crystalline protein suspension suitable for pulmonary delivery.

There have been no methods reported to produce crystalline particles for the aerosol delivery of proteins. There are several physical and chemical stability issues with proteins in aerosol generating devices such as aggregation, hydrolytic decomposition, adsorption to device surfaces and decreased respiratory fraction. Protein suspensions used in aerosol studies to date have been prepared using jet milling or spray drying processes in attempts to get uniform particle size. These techniques are relatively harsh. Shear force generated in these processes can cause protein degradation, oxidation and denaturation [Niven, R. W., Pharm. Tech., July, 72–81(1993)]. Whereas, crystallization processes are relatively mild, and they are known to protect and stabilize homogeneous protein preparations.

There has been a report of problems with the stability of interferon solutions in an ultrasonic nebulizer [Sato Y. et al., A comparison of 28 kHz and 160-kHz Ultrasonic Aerosolization of interferon-Alpha J. Aer. Med. 5,59–64(1992)].

The human interferon alphas are a family of proteins comprising at least 24 subspecies [Zoon K. C., *Interferon* 9, 1–12 (1987),Gresser I., ed. Academic Press, New York]. They were originally described as agents capable of inducing an antiviral state in cells but are known as pleiotropic lymphokines affecting many functions of the immune system [(Opdenakker, et al., *Experimentia* 45, 513–520 (1989))]. Apart from their in vitro biological activities the human alpha are currently used for several important indications including hairy cell leukemia, Kaposi Sarcoma, venereal warts, chronic hepatitis [*IntronA (interferon alpha-2b) Clinical status* (1989) Proceedings from satellite symposium at the 5th European Conference on Clinical Oncology, London, U.K. September 1989].

Several forms of crystalline human interferon alpha-a have been reported. Miller et al., Science, 215, 689–690 (1982): Kung et al., U.S. Pat. No. 4,672,108: Weissmann, The Cloning of Interferon and other Mistakes, In: Interferon 1981, Ion Gresser, ed., Academic Press, New York, 101–134: Weissmann, *Phil. Trans. R. Soc. Lond.*, B299,7–28 (1982): Nagabhushan, et al, Characterization of genetically Engineered alpha-2 Interferon, In: *Interferon: Research, Clinical Application and Regulatory Consideration*, Zoon et al., Elsevier, N.Y. 79–88 (1982). These publications describe methods for crystallizing interferon alpha-2 from polyethylene glycol at low temperature or from a phosphate buffer solution by adjusting the pH or temperature. These methods normally provide needle-shaped crystals. The Miller et al. article also mentions crystalline alpha-2 in a "prismatic form". In U.S. Pat. No. 5,460,956; Method for preparing Interferon Alpha-2b Crystals, conditions for producing monoclinic prismatic crystals of interferon alpha-2b from solutions of ammonium sulfate in vapor diffusion hanging drop experiments at 22° C. are disclosed. Methods for the preparation of zinc-interferon crystals are disclosed in U.S. Pat. No. 5,441,734. The patent details methods of crystallization involving temperature induction, vapor diffusion or dialysis. All these methods involve crystallization of a soluble zinc-interferon complex. Crystallization only occurs under defined conditions such as growth medium, pH, protein concentrations and temperature. The resulting crystals are either a cubic or needle habit. These crystals have desirable solubility properties in drug delivery systems: limited solubility at 37° C., particle size <100 μm and stability at room temperature in solutions suitable for clinical formulations.

EXAMPLE 1

Crystallization of Zinc Interferon Alpha

The interferon alpha-2 employed was recombinant human interferon alpha-2b expressed in E. coli as described in Weissmann, et al. Science, 209,1342(1980). The cells were cultured, harvested and extracted as previously reported in Leibowitz, P. et al (1982) U.S. Pat. No. 4,315,852. The resulting extract was purified by a combination of conventional purification steps: ethanol extraction, matrix gel blue ligand affinity chromatography, ion exchange and gel filtration chromatography. The resulting purified interferon alpha-2b preparation was dialyzed against either USP grade water or 0.1% trifluoroacetic acid solution and lyophilized as either the free base or trifluoroacetate salt respectively.

A zinc-interferon soluble complex was crystallized using a temperature induction method. Lyophilized interferon alpha-2b was dissolved in a zinc acetate/sodium acetate growth medium at 4° C. Using a programmable temperature chamber, the temperature was raised from 4° C. to 22° C. over 6 hours. The temperature was maintained at 22° C. for 5 days. Microscopic inspection of the resulting crystalline suspension identified crystalline particles ranging in size from 100 μm to less than 1 μm in diameter.

An alpha-2b interferon solution (40 mg /ml, 0.5 ml) in 35 mM sodium acetate (Mallinckrodt Inc. Paris, Ky.), pH 5.5 was dialyzed against 2.7 liters of 35 mM sodium acetate, 35 mM zinc acetate (Fisher Scientific, Springfield, N.J.), pH 5.5. The solution was centrifuged at 1,500 g force for 10 minutes at 4° C. (to remove particulate matter). The resulting supernatant was adjusted to pH 6.0 using 1 N sodium hydroxide dropwise at 2–4° C. and re centrifuged in a Sorval model RT6000B refrigerated centrifuge at 1,500 g force for 10 minutes at (to remove particle matter) at 4° C. In a Hotpack programmable temperature chamber model # 435314, the batch was temperature ramped from 4°–22° C. using a linear gradient over 6 hours. After 5 days at 22° C., the batch was inspected microscopically for crystal growth at room temperature, a suspension of crystalline particles in a range of 100 μm to less than 1 μm was observed microscopically.

EXAMPLE 2

Isolation of Crystalline Interferon Alpha Particles Having a Predetermined Size The suspension from Example 1 was vortexed to obtain a uniform suspension. After 1 hour of settling, the suspended solution was separated by aspiration from the settled solid. The average particle diameter was 1.8 μm with standard deviation of 0.25 μm for the 1 hour suspension after harvest sample by morphometric analysis. The 1 hour suspension was incubated at 22° C. for 6 hours. The suspension was separated from the settled solid. Morphometric analysis of the particles after harvest of the 6 hour sample was 1.5 μm mean diameter with a standard deviation of 0.4 μm. The six hour resulting suspension was incubated for an additional 24 hours. The suspension was separated from the settled solid by aspiration. In general, the size of crystals remaining in suspension decreased over time settling.

EXAMPLE 3

Analysis of Crystalline Particle Size

The Brinkman particle size analyzer, the classical instruments used for the measurement of the range and distribution of particles within a liquid suspension was used to get an accurate measurement of size and distribution of particles. An aliquot of the 24 hour suspension after harvest was analyzed in a stirred cell of the Brinkman particle size analyzer. The mean diameter was found to be 0.78 μm with a standard deviation of 0.19 μm by volume distribution.

EXAMPLE 4

Tests were performed to confirm the crystallinity of the 24 hour settled sample including birefringence and X-ray diffraction analysis. A birefringence test was performed to distinguish amorphous vs crystalline particles. The 24 hour suspension was examined on a polarized microscope. Crystalline particles glow as a result of the plane of polarization that occurs when light passes through the crystal. True amorphous precipitates do not affect the polarization in a coherent fashion and will not glow [*Crystallization of Nucleic Acids and Proteins A Practical Approach*, eds., Ducruix, A. and Geige, R., Oxford University Press, New York, N.Y., 64 (1992)]. The 24 hour suspension glowed upon microscopic inspection under polarized light. The particles appeared to be consistent with crystalline particles described as spherulites. Spherulites are radially symmetric aggregates of microscopic needles. The overall shape and profile of the particles were very similar to the spherulite particles illustrated in [*Crystallization of Nucleic Acids and Proteins A Practical Approach*, eds., Ducruix, A. and Geige, R., Oxford University Press, New York, N.Y., 64, page 3 (1992)].

EXAMPLE 5

An aliquot of the crystalline suspension was centrifuged in a 1.5 mm glass X-ray capillary tube and examined on a rotating anode X-ray system. The observed pattern of concentric rings is consistent with a crystalline suspension. A lyophilized amorphous form of interferon alpha-2b was also analyzed by X ray diffraction analysis in a comparable experiment. There were no observed concentric rings observed. This result is consistent with an amorphous solid sample.

EXAMPLE 6

Further tests were performed to establish the protein and interferon content of the sample. The interferon and protein content of the 24 hour suspension was determined from a sample which was centrifuged and the pellet was dissolved in 0.2M EDTA solution. The protein content of the 24 hour suspension was determined to be 0.11 mg/ml using the Bradford assay. The Bradford Assay is a modification of the standard Coomassie blue dye binding assay so that the absorbance is directly proportional to protein concentration. Details are in Bradford, M. (1976) Anal. Biochem. 72, 248–254.

Protein Content/Specific Biological Activity 1 ml aliquot of decanted 24 hour settling suspension was centrifuged at 10,000 rpm for 15 min. The supernatant was decanted and the pellet was resuspended in 35 mM sodium acetate, 35 mM zinc acetate, pH 6.1 at 22° C. The suspension was centrifuged at 10,000 rpm for 15 minutes and the supernatant was decanted. The resulting pellet was dissolved in 200 μl of 0.2 M EDTA solution. The protein content was 0.5 mg/ml using a Bradford protein assay. An aliquot of the 0.2M EDTA solution was analyzed for interferon content against interferon alpha-2b as a standard.

Using an ELISA method, the interferon content was measured at two concentrations run in duplicate. A specific activity of $2 \times 10^8$ IU/mg protein was found and is comparable to the specific activity of the interferon standard run within the assay.

Enzyme-Linked Immunoadsorbant Assay (ELISA)

Interferon content was measured by adding aliquots to a microtiter plate coated with sheep anti-alpha interferon antibody (Mab; Sheep 777 anti IFN, Schering-Plough Corp.). The plates were covered and the samples were incubated for at least two hours at ambient temperature. Interferon or related substances reacted with the antibody. A murine monoclonal antibody; (Mab;7N4-1 Schering-Plough Corp.) was added to bind the interferon. The concentration of the bound Mab was proportional to the amount of interferon added. The bound Mab was measured by using anti-murine IgG conjugated to biotin (Jackson Immunoresearch,#515-065-062) followed by streptavidin conjugated to peroxidase (Jackson Immunoresearch, # 016-030-084). 3,3',5,5'-Tetramethylbenzidine Dichloride (TMB) (Sigma,# T55525) was added for color development and the absorbance at 450 nanometers was used to determine the concentration of interferon. Comparisons were made with known amounts of interferon Alpha-2b treated and assayed under the same conditions. Results were expressed in international units per millimeter (IU/ml).

EXAMPLE 7

A sample of the 24 hour settled sample from Example 1 was centrifuged and resuspended in 5 mM sodium acetate, pH 6.1 buffer containing 0.1% Tween 80. There was no change observed in the microscopic observation of the sample after one month.

EXAMPLE 8

Crystallization of Zinc Interferon Alpha with Stirring

Alpha-2b interferon lyophilized powder (14 mg ) was dissolved in 1.0 ml of 60 mM sodium acetate, 20 mM zinc acetate, pH 6.1 at 4° C. The solution was centrifuged at 1,500 g force for 10 minutes at 4° C. (to remove particulate matter). The resulting supernatant was placed in a 5 dram glass vial with a PGC Scientific (Gaithersburg, Md.) Teflon coated stirring bar size 2×5 mm, catalog #77-8634-45. The solution was stirred at a setting of 2 on a Fisher (Fair Lawn, N.J.) Thermix magnetic stirrer model #120S at 4° C. In a Hotpack programmable temperature chamber model # 435314, the batch was temperature ramped from 4°–22° C. using a linear gradient over 1 hour. After 4 days at 22° C., the resulting crystalline suspension was inspected microscopically for crystal growth at room temperature. Microscopically, the crystalline a suspension consisted of crystalline particles in a range of 10 micrometers to less than 1 μm.

EXAMPLE 9

Pulmonary Delivery Formulation

Crystalline suspension ($10–50 \times 10^6$ international units) from example above is re-suspended in sterile filtered 5 mM sodium acetate, pH 6.1, 0.1% Tween 80 (pharmaceutical grade). The resulting suspension can be utilized in numerous commercially available nebulizers such as a Collison nebulizer model # CN-24, 3-jet modified nebulizer from BGI Incorporated (Waltham, Mass.).

We claim:

1. A crystalline interferon alpha-2, wherein particles of said crystalline interferon alpha-2 have a diameter ranging from 0.7 micrometer (μm) to about 7.0 μm, are directly formed by a crystallization method which results in the formation of particles having such a diameter, and have predictable properties of uniformity, homogeneity, stability, bioavailability, and dissolution relative to milled or spray dried particles.

2. The crystalline interferon alpha-2 of claim 1 wherein said particles have a diameter of less than 5 μm.

3. The crystalline interferon alpha-2 of claim 1 wherein the interferon alpha-2 is interferon alpha-2b.

4. The crystalline interferon alpha-2 of claim 1 which is crystalline zinc interferon alpha-2.

5. The crystalline interferon alpha-2 of claim 4 wherein the interferon alpha-2 is interferon alpha-2b.

6. A composition comprising the crystalline interferon alpha-2 of claim 1 and a pharmaceutically acceptable carrier.

7. The composition of claim 6 wherein the pharmaceutically acceptable carrier is a carrier for an aerosol composition.

8. The crystalline interferon alpha-2 of claim 1 wherein said particles have a spherulite morphology.

9. The crystalline interferon alpha-2 of claim 1 wherein said particles appear crystalline by a birefringence test or by X-ray diffraction analysis, or both.

10. The crystalline interferon alpha-2 of claim 1 wherein said particles have a diameter in the range of 780 nanometers.

11. The crystalline interferon alpha-2 of claim 1 wherein said particles have a mean diameter of 1.8 μm with a standard deviation of 0.25 μm.

12. The crystalline interferon alpha-2 of claim 1 wherein said particles have a mean diameter of 1.5 μm with a standard deviation of 0.4 μm.

13. The crystalline interferon alpha-2 of claim 1 wherein said particles have a mean diameter of 0.78 μm with a standard deviation of 0.19 μm.

14. A method for preparing a suspension of crystalline interferon alpha-2 particles wherein the particles have a diameter of 0.7 to 7 μm comprising:

(a) crystallizing interferon alpha-2 in solution to form a suspension of crystalline interferon alpha-2;

(b) mixing the suspension so as to produce a homogenous suspension of crystalline interferon alpha-2;

(c) sedimentating the homogenous suspension of crystalline interferon particles under conditions wherein only crystalline interferon alpha particles having a particle size ranging from 0.7 to 7.0 μm are present in a supernatant suspension.

15. The method of claim 14 wherein the diameter of the crystalline interferon alpha-2 particles in the supernatant suspension is less than about 5.0 μm.

16. The method of claim 14 wherein the solution of interferon alpha-2 is agitated during crystallization.

17. The method of claim 14 wherein after the suspension of is mixed the suspension is allowed to settle such that particles having a diameter greater than about 7.0 µm settle to a bottom pellet layer and particles having a diameter of less than or equal to 7.0 µm remain in a supernatant suspension.

18. The method of claim 17 further comprising allowing the crystalline interferon alpha-2 particles to further sedimentate until only crystalline particles having a predetermined diameter are present in the supernatant suspension.

19. The method of claim 18 wherein the crystalline alpha-2 particles which remain in the supernatant suspension have an average of less than about 5 µm.

* * *